United States Patent
Krause et al.

(10) Patent No.: US 6,294,570 B1
(45) Date of Patent: Sep. 25, 2001

(54) ENDOSULFAN MICROCAPSULE DISPERSION

(75) Inventors: Hans-Peter Krause; Thomas Maier, both of Hofheim; Jan Nicolaas Bremmer, Kriftel, all of (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/265,111

(22) Filed: Mar. 9, 1999

(51) Int. Cl.⁷ ............................. A01N 43/02; A01N 25/00
(52) U.S. Cl. .................... 514/431; 424/405; 424/406; 424/490; 424/497; 424/498; 424/678; 514/430; 514/449; 514/450; 514/769; 514/772.1; 514/772.3; 514/974
(58) Field of Search ................................. 424/400, 405, 424/406, 490, 497, 498, 678; 514/430, 431, 769, 772.1, 772.3, 974, 449, 450

(56) References Cited

U.S. PATENT DOCUMENTS

| | | | |
|---|---|---|---|
| 3,577,515 | * | 5/1971 | Vandegaer ............................. 424/497 |
| 4,140,516 | * | 2/1979 | Sher ...................................... 504/220 |
| 4,230,809 | | 10/1980 | Heinrich ................................. 521/65 |
| 4,938,797 | * | 7/1990 | Hässlin et al. ........................ 504/359 |
| 5,163,994 | * | 11/1992 | Klimesch et al. .................... 504/361 |
| 5,549,903 | * | 8/1996 | Marcus ................................. 424/408 |
| 5,733,848 | * | 3/1998 | Luteri ................................... 504/359 |
| 5,780,389 | * | 7/1998 | Krause et al. ........................ 504/359 |
| 5,866,153 | * | 2/1999 | Hasslin et al. ....................... 424/408 |

FOREIGN PATENT DOCUMENTS

| | | | |
|---|---|---|---|
| 2767017-A1 | * | 7/1979 | (DE) . |
| 0134674 | | 3/1985 | (EP) . |
| 0183999 | | 6/1986 | (EP) . |
| 0368576 | | 5/1990 | (EP) . |
| 0619073 | | 10/1994 | (EP) . |
| WO 95/23506 | | 9/1995 | (WO) . |
| WO-96/09760-A1 | * | 4/1996 | (WO) . |

OTHER PUBLICATIONS

Patent Abstracts of Japan No. 06256116A published Sep. 13, 1994.

* cited by examiner

Primary Examiner—Jose' G. Dees
Assistant Examiner—Frank Choi
(74) Attorney, Agent, or Firm—Frommer Lawrence & Haug LLP

(57) ABSTRACT

Aqueous endosulfan microcapsule dispersions in which the dispersed microcapsules comprise endosulfan, an organic solvent or solvent mixture and a capsule-forming material based on isocyanate prepolymers and the aqueous phase which represents the dispersion medium comprises surfactants, a water-soluble inorganic salt with or without other formulation aids, which include a relatively small amount of capsule-forming material, and a process for their preparation.

9 Claims, No Drawings

ENDOSULFAN MICROCAPSULE DISPERSION

BACKGROUND OF THE INVENTION

Numerous patent applications have already described the microencapsulation of pesticidal active ingredients. Formulations of this type can, for example, release the encapsulated active ingredient in a delayed manner and various undesirable properties of the active ingredient, such as toxicity to the user or leachability into ground water, can be beneficially influenced by this means.

DESCRIPTION OF THE RELATED ARTS

For example, EP-A-134 674 discloses the reduction of skin toxicity of difonate in rabbits, EP-A-183 999 discloses the reduction of fish toxicity of permethrin, EP-A-368 576 discloses the reduction of the toxicity of chlorpyrifos in carp, JP-A-6-256116 discloses the reduction of skin toxicity of fenobucarb and WO-A-95/123506 discloses the reduction of fish toxicity and of food toxicity in mice.

Of the different variants of microcapsules, capsule dispersions have proved to be particularly useful. They may be produced by enveloping, for example, water-insoluble active ingredient in an aqueous environment with a polymer skin, stabilizing the resulting dispersion, if appropriate, with dispersants and producing a water-diluteable concentrate directly in this manner. With these formulations, as with all multiphase formulations, care must be taken to ensure that thickening, coagulation or sediment formation does not occur during storage; the user must at least, with reasonable effort, be able to reverse these changes which diminish quality. It is in the nature of things that active ingredients of high density are therefore the most difficult to process to form microcapsule dispersions. Requirements of physical stability must be complied with by suitable composition of the aqueous carrier phase.

The pesticide-containing capsules are subject to two further essential, contradictory requirements. On the one hand, a sufficiently stable coating must ensure that the sought-after goal of the encapsulation is achieved, namely the binding of the active ingredient to the capsule interior. This means, for example in the case of insecticides toxic to homoiotherms, that the active ingredient is not released from its sealing until the user has typically diluted and applied the formulation and the sprayed coating has dried onto the target surface.

On the other hand, said coating must on no account be so strong that the active ingredient exits too slowly after application. The lowest limit of the release rate in this case is predetermined by many factors, e.g. physicochemical conditions, biological mode of action, type of the pest organism to the controlled, tolerance of plant protection residues in the treated crop.

The insecticidal active ingredient endosulfan is included, on account of its toxicity, among those requiring appropriate labelling in accordance with the German Regulation on Hazardous Substances. However, endosulfan has a great number of merits, so that it has nevertheless to a greater extent established itself as the standard insecticide in various crops. Thus, there has long been a requirement for a commercial form of endosulfan in the form of a microcapsule dispersion which satisfies said requirements.

The most usual way of building up said capsule wall around the active ingredient to be enveloped is an interfacial polymerization in oil-in-water emulsions, the organic phase including, in addition to the active ingredient, an oil-soluble prepolymer having free isocyanate groups.

U.S. Pat. No. 3 577 515 describes how, after addition of water-soluble polyamines, the droplet surface in such emulsions cures as a result of addition to the prepolymers containing the isocyanate groups. This forms a polyurea outer wall.

U.S. Pat No. 4 140 516 discloses that, even in the absence of external water-soluble amines, microcapsules having outer wall of the polyurea type can be produced by permitting partial hydrolysis in the emulsion of the prepolymer bearing the isocyanate functions. In the course of this, some of the amino groups are reformed from the isocyanate groups and, as a result of internal polyaddition with subsequent curing, the desired capsule wall is likewise formed. The use of tolylene diisocyanate, hexamethylene diisocyanate, methylenebis(phenyl isocyanate) and of its higher homologs is described. If curing is to be performed using an external polyamine, this usually originates from the group consisting of ethylenediamine, propylenediamine, hexamethylenediamine, diethylenetriamine and tetraethylenepentamine.

Formulations including microencapsulated endosulfan have already been described several times in the patent literature.

DE-A-2 757 017 relates to internally structured microcapsules whose wall material has the nature of a mixed polymer crosslinked by urea and urethane moieties. The active ingredient is situated in the interior of the capsule, dissolved in an organic solvent. Typically, to make up the capsule wall here, 10% of prepolymer, based on the total formulation, is required. There is no information on the reduction in acute oral toxicity by this type of formulation.

The same prepolymer is also used in WO-A-96/09760 to encapsulate endosulfan. Although good insecticidal activity is described, no advantage is described with respect to unwanted toxic action.

WO-A-95/23506 relates to endosulfan-charged polyurea microcapsules in which the active ingredient is present as a cooled melt. As prepolymer, a mixture of methylenebis (phenyl isocyanate) and its higher homologs is described; the amount of prepolymer used is over 6%, based on the total formulation. Curing is performed using a mixture of polyamines. Apart from the data on the greatly reduced toxicity of this type of formulation, no indications are given there of advantages in biological activity or with respect to residues.

There continued to be, therefore, a desire for an insecticidal formulation including microencapsulated endosulfan, which formulation complies with the following requirements:

- simple nonhazardous preparation
- good storage stability
- reduced toxicity to the user and to useful organisms
- good initial biological activity
- no risk of increased residues of unreleased active ingredient on the treated plant parts.

It has now surprisingly been found that a microcapsule dispersion which is prepared by the interfacial polymerization process known per se and includes up to 30% by weight or more of endosulfan, preferably approximately 300 to 330 g of endosulfan/l, complies with the abovementioned requirements if, for its preparation, relatively small amounts of an isocyanate-containing prepolymer (of the order of magnitude of approximately 1% by weight) are used, in addition to any water-soluble diamine required. The very small amount of prepolymer forming the capsule wall means in fact that the onset of the insecticidal activity is not retarded under practical conditions. Addition of a sufficiently large amount of a water-soluble inorganic salt such as sodium chloride to the aqueous phase, and an associated increase in density, can prevent the microcapsules from sedimenting after a certain time and possibly forming a bottom sediment which is difficult to redisperse.

Microcapsule dispersions of this type, because of their favorable acute toxicity to homoiotherms, permit the toxicological classification "harmful", and surprisingly exhibit—if they contain calcium chloride as density-increasing agent—a considerably lower fish toxicity than those microcapsule dispersions which do not contain calcium chloride. Commercial emulsifiable concentrates are known to have a by far still higher fish toxicity.

SUMMARY OF THE INVENTION

The invention relates to aqueous endosulfan microcapsule dispersions in which the dispersed microcapsules comprise endosulfan, an organic solvent or solvent mixture and a capsule-forming material based on isocyanate prepolymers and the aqueous phase which represents the dispersion medium comprises surfactants with or without other formulation aids, and which microcapsule dispersion contains, based on the total dispersion, 20–40% by weight of endosulfan, 10–35% by weight of organic solvent or solvent mixture, capsule-forming material based on 0.5–5% by weight of isocyanate prepolymers, 0.2–5% by weight of one or more surfactants selected from the group consisting of emulsifiers and dispersants and a water-soluble inorganic salt, the salt content being selected in such a manner that the density of the aqueous phase is between 1.05 and 1.45 kg/l.

DESCRIPTION OF THE INVENTION

In the microcapsule dispersions according to the invention, use can be made of organic solvents or their mixtures selected from the group consisting of the N-alkylamides of fatty acids, N-alkyllactams, esters of fatty acids and aromatic hydrocarbons, lower-alkyl-substituted naphthalene derivatives being particularly suitable.

Commercially available solvents which are suitable according to the invention are, for example, ®Solvesso 200 (1), butyl diglycol acetate, ®Shellsol RA (2), ®Acetrel 400 (3), ®Agsolex 8 (4), ®Agsolex 12 (5), ®Norpar 13 (6), ®Norpar 15 (7), ®Isopar V (8), ®Exsol D 100 (9), ®Shellsol K (10) and ®Shellsol R (11), which have the following compositions:

(1) Mixtures of alkylated napthalenes, boiling range 219–282° C., manufacturer: Exxon.
(2) Mixtures of alkylated benzenes, boiling range 183–312° C., manufacturer: Shell.
(3) High-boiling mixture of aromatics, boiling range: 332–355° C., manufacturer Exxon.
(4) N-Octylpyrrolidone, boiling point (0.3 mm Hg) 100° C., manufacturer: GAF.
(5) N-Dodecylpyrrolidone, boiling point (0.3 mm Hg) 145° C., manufacturer: GAF.
(6) Aliphatic hydrocarbons, boiling range: 228–243° C., manufacturer: Exxon.
(7) Aliphatic hydrocarbons, boiling range: 252–272° C., manufacturer: Exxon.
(8) Aliphatic hydrocarbons, boiling range: 278–305° C., manufacturer: Exxon.
(9) Aliphatic hydrocarbons, boiling range: 233–263° C., manufacturer: Exxon.
(10) Aliphatic hydrocarbons, boiling range: 192–254° C., manufacturer: Shell.
(11) Aliphatic hydrocarbons, boiling range: 203–267° C., manufacturer: Shell.

Mixtures of these solvents with one another are also suitable. In particular, butyl diglycol acetate, ®Acetrel 400, ®Agsolex 8 and ®Agsolex 12 are readily usable. ®Solvesso 200 is particularly preferred.

The active ingredient endosulfan is present in solution in this solvent, more precisely such that the concentration of active ingredient based on the total formulation is between 20 and 40% by weight, preferably between 20 and 35% by weight. Particular preference is given to approximately 300 to 330 g of endosulfan/l of total formulation.

The capsule-forming material of which the walls of the microcapsules are made is preferably produced starting from oil-soluble prepolymers containing isocyanate groups, which are a group of industrial mixed products, which consist in each case of polyisocyanates based on condensates of aniline and formaldehyde. These industrial mixed products differ from one another in the degree of condensation and, possibly, in chemical modifications. Important characteristics for the user are viscosity and content of free isocyanate groups. Typical commercial products here are the ®Desmodur brands (Bayer AG) and ®Voranate brands (Dow Chemicals). It is essential for the invention that the amount of prepolymer containing isocyanate groups used is $\leq 5\%$ by weight based on the total formulations; preference is given to 0.5–5% by weight, in particular 1–2% by weight.

The capsule-forming material is formed by curing the isocyanate prepolymer either in the presence of water at 0–95° C., preferably 20–65° C. or, preferably, with the required amount of a diamine.

If the microcapsules are formed with the inclusion of diamines, those which are suitable are, for example, alkylenediamines, dialkylenetriamines and trialkylenetetramines whose carbon chain units contain between 2 and 8 carbon atoms. Preference is given to hexamethylenediamine. In this case, amounts can be used which are either in a stoichiometric ratio to the amount of isocyanate prepolymer used or are preferably in up to threefold excess, in particular in up to two-fold excess.

The aqueous phase of the formulations according to the invention include surface-active formulation aids selected from the group consisting of emulsifiers and dispersants. They originate from a group which includes, for example, the families poly(vinyl alcohols), poly(alkylene oxides), the condensation products of formaldehyde with naphthalenesulfonic acids and/or phenols, polyacrylates, the copolymers of maleic anhydride with alkylene alkyl ethers, ligninsulfonates and polyvinylpyrrolidones. These substances are used at 0.2 to 5% by weight, preferably at 0.5 to 2% by weight, in each case based on the total dispersion.

Preferred poly(alkylene oxides) are block copolymers whose molecular center is formed by a poly(propylene oxide) block, but the molecular periphery in contrast is formed by poly(ethylene oxide) blocks. Particular preference is given in this case to substances in which the polypropylene block has a molar mass of 2000–3000, and the poly(ethylene oxide) blocks make up 60 to 80% of the total molar mass. A substance of this type is marketed, for example, by BASF Wyandotte under the name ®Pluronic F87.

Other suitable dispersants are calcium ligninsulfonate, highly refined sodium ligninsulfonate (e.g. ®Vanisperse CB from Borregard), dispersant SI and dispersant SS from Hoechst AG, naphthalenesulfonic acid/formaldehyde condensation product, sodium salt (e.g. ®Morwet D 425 from DeSoto or ®Tamol NN 8906 from BASF), sodium polycarboxylate (e.g. ®Sopropon T 36 from Rhône Poulenc).

Suitable poly(vinyl alcohols) are prepared by partial saponification of poly(vinyl acetate). They have a degree of hydrolysis of 72 to 99 mol% and a viscosity of 2 to 18 cP (measured in 4% strength aqueous solution at 20° C., in accordance with DIN 53 015). Preferably, partially saponified poly(vinyl alcohols) are used having a degree of hydrolysis of 83 to 88 mol% and low viscosity, in particular 3 to 5 cP.

The aqueous phase of the formulations according to the invention includes, if appropriate, at least one further formulation aid selected from the group of wetting agents, antifreezes, thickeners, preservatives and constituents increasing density.

Suitable wetting agents belong, for example, to the classes of substances alkylated naphthalenesulfonic acids, N-fatty acyl N-alkyltaurides, fatty acylamidoalkylbetaines, alkyl polyglycosides, alpha-olefinsulfonates, alkylbenzenesulfonates, the esters of sulfosuccinic acid and fatty alkyl sulfates (unmodified or modified by alkyleneoxy groups). Their content here is between 0 and 5% by weight, preferably between 0 and 2% by weight, based on the total formulation.

Suitable commercial products are, for example, ®Darvan No. 3, ®Vanisperse CB, ®Luviskol K 30, Reserve C, ®Forlanit P, ®Sokalan CP 10, ®Maranil A, ®Genapol PF40, ®Genapol LRO, tributylphenol polyglycol ethers, such as ®Sapogenat T brands (Hoechst), nonylphenol polyglycol ethers, such as the ®Arkopal N brands (Hoechst) or tristyrylphenol polyglycol ether derivatives.

As preservatives, the following compounds can be added to the aqueous formulations: formaldehyde or hexahydrotriazine derivatives, such as ®Mergal KM 200 from Riedel de Haen or ®Cobate C from Rhône Poulenc, isothiazolinone derivatives, such as ®Mergal K9N from Riedel de Haen or ®Kathon CG from Rhom & Haas, 1,2-benzisothiazolin-2-ones, such as ®Nipacide BIT 20 from Nipa Laboratories GmbH or ®Mergal K10 from Riedel de Haen or 5-bromo-5-nitro-1,3-dioxane (®Bronidox L from Henkel). The content of these preservatives is at most 2% by weight based on the total formulation.

Suitable antifreezes are, for example, monohydric or polyhydric alcohols, glycol ethers or urea, in particular calcium chloride, glycerol, isopropanol, propylene glycol monomethyl ether, di- or tripropylene glycol monomethyl ether or cyclohexanol. The content of these antifreezes is at most 20% by weight based on the total formulation.

Thickeners can be inorganic or organic; they can also be combined. Suitable thickeners are, for example, those based on aluminum silicate, xanthan, methylcellulose, polysaccharide, alkaline earth metal silicate, gelatin and poly(vinyl alcohol), such as ®Bentone EW, ®Veegum, ®Rodopol 23 or ®Keizan S. Their content is 0–0.5% by weight based on the total formulation.

Constituents which can serve to increase the density of the aqueous phase are water-soluble salts of alkali metals and alkaline earth metals and ammonium salts or mixtures thereof; preference is given to calcium chloride. The amount of salt depends on the specific gravity which the aqueous phase is to have in each case, that is densities between 1.05 and 1.45 kg/l, preferably between 1.10 and 1.40 kg/l, and particularly preferably 1.15 and 1.35 kg/l. Preference is given to amounts which when added make the density of the aqueous phase approximately equal to the density of the organic phase.

The invention also relates to a process for preparing the microcapsule dispersions according to the invention, which involves firstly preparing a coarse preemulsion of an organic and aqueous phase (without diamine), and then subjecting this to shear forces, by passing it, preferably, through a continuous mixer element, for example a static mixer, a toothed colloid mill or the like. The fineness of the emulsified oil droplets which is required for later microcapsule formation is not produced until this step. Finally, if appropriate after addition of a diamine, curing is performed by polymerization reaction in the entire volume of substance.

The process can be carried out semicontinuously on a pilot plant scale and production scale.

The examples below serve to illustrate the invention without restricting it thereto.

A. Formulation Examples

EXAMPLES 1–5

Pilot-Plant Experiments

A solution was prepared in each case from 27 kg of technical-grade endosulfan and 23 kg of ®Solvesso 200 in a 200 l stirred tank equipped with an anchor agitator, and was run off into a storage vessel.

The respective aqueous phase (see below in Table 1 for the composition of the individual examples) was then prepared in the same stirred tank by charging it with water and introducing the respective aids with stirring. The mixture continued to be stirred slowly until complete dissolution. The agitator speed was then increased to 70 rpm and the freshly prepared mixture of the organic phase prepared as specified above with 1 kg of ®Voranate M220 was added rapidly.

After further stirring for a short times the agitator was turned off and the resulting yellowish coarse emulsion was run off into a storage vessel via a toothed colloid mill, a pale fine emulsion being formed, whose droplets had a diameter of 2–15 $\mu$m, depending on the setting of the toothed colloid mill. This fine emulsion was returned to the stirred tank and the agitator again started at 70 rpm. 2.5 kg of a 40% strength aqueous hexamethylene solution was added and the mixture was stirred for a further 4 hours at 30 rpm.

TABLE 1

| | Examples (all quantities in kg) | | |
|---|---|---|---|
| | 1,2 | 3,4 | 5 |
| ® Mowiol 3/83 | 2.00 | 2.00 | 1.00 |
| ® Pluronic F87 | 1.80 | 1.80 | 1.80 |
| ® Morwet D425 | 0.50 | | |
| ® Galoryl DT12O | | 0.50 | |
| ® Soprofor FL | | | 2.00 |
| ® Rhodopol 23 | 0.10 | 0.10 | 0.10 |
| ® Mergal K9N | 0.10 | 0.10 | 0.10 |
| ® Antimussol UP | 0.10 | 0.10 | 0.10 |
| CaCl$_2$ anhydrous | 12.20 | 11.00 | |
| Glycerol, technical grade | 4.00 | 4.00 | |
| Water | 25.70 | 26.90 | 41.40 |

The microcapsules obtained in dispersion have a mean diameter which is dependent not only on the composition of the formula but also on the speed of rotation of the rotor in the mill and on the setting of the spacing between rotor and stator (the "grinding gap"). This is described in more detail in Table 2. The viscosity values reported were determined using a rotary viscometer.

TABLE 2

| Example | Speed of rotation (rpm) | Grinding gap | Viscosity/mPas at 144 s$^{-1}$ | Capsule diameter ($\mu$m) |
|---|---|---|---|---|
| 1 | 3000 | 3 | 840 | 2.8 |
| 2 | 1500 | 3 | 1100 | 5.1 |
| 3 | 1500 | 1 | 500 | 9.0 |
| 4 | 1500 | 1 | 510 | 8.7 |
| 5 | 3000 | 3 | 140 | 2.5 |

EXAMPLE 6

A microcapsule dispersion was prepared as in Examples 1–5, except that a continuous mixing step was not provided. The aqueous phase comprised 2.1 kg of ®Mowiol 3/83, 1.8 kg of ®Pluronic F 87, 0.5 kg of ®Morwet D425, 4 kg of technical-grade glycerol(86.5% pure) and 100 g each of ®Rhodopol 23 and ®Mergal K9N in 36.8 g of water. This aqueous phase was charged into a stirred tank equipped with an anchor agitator and the organic phase of 27 kg of technical-grade endosulfan, 24 kg of Solvesso 200 and 1 kg of prepolymer ®Voranate M220 was poured in via a drum tilter at room temperature with stirring. After stirring for 30 min, 2.5 kg of a 40% strength aqueous hexamethylenediamine solution were added and the mixture was or a further 4 h.

Microcapsules having a mean diameter of 14.9 $\mu$m were produced in this manner.

EXAMPLE 7

A microcapsule dispersion was prepared as in Example 6, except that a propeller agitator was used instead of the anchor agitator. Under otherwise identical conditions, microcapsules having a mean capsule diameter of 4.1 $\mu$m were then produced.

EXAMPLE 8

Comparison Example

For this microencapsulation experiment, the prepolymer used was a substance which was produced by reacting 8 mol of tolylene diisocyanate with hexane-1,2,6-triol: butane-1, 3-diol: poly(propylene glycol) 1000 in a molar ratio of 3:1:1 and, for further use, was dissolved in a 1:1 mixture of n-butyl acetate and xylene, in which the prepolymer was present in a 50% strength solution (described in DE-A2757017).

A microcapsule dispersion was prepared as described in Example 1, except that 36.4 parts of water and 3 parts of the abovementioned prepolymer solution were used, with no diamine used for curing. Furthermore, the mixture was further stirred for 15 h at room temperature. The microcapsules of the dispersion produced had a mean diameter of 17 $\mu$m, and the viscosity in the rotary viscometer was 350 mPas at a shear rate of 144 s$^{-1}$.

EXAMPLES 9, 10 and 11

Respective microcapsule dispersions were prepared on laboratory scale using the formulas of Examples 1, 3 and 5, by charging 46.5 parts of the abovedescribed aqueous phase and introducing 51 parts of the complete organic phase into the aqueous phase with stirring at 300 rpm. The agitator was then set to 2000 rpm and stirring was continued initially for 30 seconds at 2000 rpm.

The speed of rotation was then reduced to 300 rpm, 2.5 parts of a 40% strength aqueous solution of hexamethylenediamine were added and the mixture was further stirred for 1 minute. The speed of rotation was finally further decreased to 50 rpm and stirring was continued for 4 h.

The results are reproduced in Table 3.

TABLE 3

| Example | Formula as in example | Viscosity/mPas at 144 s$^{-1}$ | Capsule diameter ($\mu$m) |
|---|---|---|---|
| 9 | 1 | 870 | 8.1 |
| 10 | 3 | 560 | 7.8 |
| 11 | 5 | 150 | 8.4 |

B. Biological Examples

EXAMPLE 12

Initial Action and Persistent Action on Aphis Fabae

Bean plants were sprayed to the point of run-off with an aqueous dilution of each specified formulation and infested with aphids immediately or 3 days after drying.

Assessment: mortality (%) at 7 days after infestation (see Table 4)

TABLE 4

| Formulation | g of active ingredient/hl | Infestation after 0 days | 3 days |
|---|---|---|---|
| Endosulfan EC35 (commercial product) | 30 | 99 | 30 |
| | 10 | 90 | 15 |
| | 3 | 0 | 0 |
| Formulation example 10 | 30 | 100 | 95 |
| | 10 | 98 | 60 |
| | 3 | 93 | 0 |

EXAMPLE 13

Initial Action Persistent Action on Heliothis Virescens

Cotton plants were sprayed with an aqueous dilution of each specified formulation at an application rate of 200 l of sprayed liquid per ha. After drying, the plants were infested with larvae of tobacco bud worm immediately or after 4 and 7 days. (See Table 5 for the result).(Assessment mortality (%) 4 days after infestation)

TABLE 5

| Formulation | g/ha | Infestation after 0 days | 4 days | 7 days |
|---|---|---|---|---|
| Endosulfan EC35 (commercial product) | 300 | 100 | 100 | 50 |
| | 100 | 100 | 70 | 20 |
| | 30 | 80 | 30 | 40 |
| | 10 | 10 | 0 | 10 |
| Formulation example 10 | 300 | 100 | 100 | 100 |
| | 100 | 90 | 100 | 100 |
| | 30 | 10 | 80 | 100 |
| | 10 | 20 | 30 | 90 |

The glasshouse experiments verify that a microcapsule formulation according to the invention is at least equivalent to a commercial EC formulation with regard to initial and persistent action.

C. Toxicological Experiments

EXAMPLE 14

Microcapsules having mean capsule diameter of 14.9 μm, prepared as described in Example 6:
$LD_{50}$ in female rats: 530 mg/kg of body weight

EXAMPLE 15

Microcapsules having mean capsule diameter of 4.1 μm, prepared as described in Example 7:
$LD_{50}$ in female rats: 315 mg/kg of body weight

EXAMPLE 16

Microcapsules having mean capsule diameter of 7.8 μm, prepared as described in Example 10:
$LD_{50}$ in female rats: greater than 200 mg/kg of body weight

EXAMPLE 17

Microcapsules having mean capsule diameter of 17 μ, prepared as described in Example 8:
$LD_{50}$ in female rats: 173 mg/kg of body weight The toxicological experiments verify the more favorable oral toxicity of the formulations according to the invention in homoiotherms over a broad range of diameters.

D. Fish Toxicity

The examples in Table 6 show that the fish toxicity of a calcium-chloride-containing microcapsule formulation according to the invention is substantially below that of microcapsule dispersions lacking calcium chloride.

TABLE 6

Fish toxicity to bluegill sunfish

| Concentration: | Mortality after | | | |
|---|---|---|---|---|
| mg of formulation/l | 24 h Animals/% | 48 h Animals/% | 72 h Animals/% | 96 h Animals/% |
| Example 18: Microcapsule dispersion lacking $CaCl_2$ (formulation example 5) | | | | |
| Control | 0/0 | 0/0 | 0/0 | 0/0 |
| 0.032 | 0/0 | 0/0 | 0/0 | 0/0 |
| 0.1 | 3/100 | 3/100 | 3/100 | 3/100 |
| Example 19: Microcapsule dispersion according to the invention (formulation example 1) | | | | |
| Control | 0/0 | 0/0 | 0/0 | 0/0 |
| 0.032 | 0/0 | 0/0 | 0/0 | 0/0 |
| 0.1 | 0/0 | 0/0 | 0/0 | 0/0 |
| Example 20: Microcapsule dispersion according to the invention (formulation example 3) | | | | |
| Control | 0/0 | 0/0 | 0/0 | 0/0 |
| 0.032 | 0/0 | 0/0 | 0/0 | 0/0 |
| 0.1 | 0/0 | 0/0 | 0/0 | 0/0 |

What is claimed is:

1. An aqueous endosulfan microcapsule dispersion in which the dispersed microcapsules comprise endosulfan, an organic solvent or solvent mixture and a capsule-forming material based on isocyanate prepolymers and the aqueous phase, which represents the dispersion medium, comprises surfactants with or without other formulation aids, and which microcapsule dispersion, based on the total dispersion, comprises:

20–40% by weight of endosulfan;
10–35% by weight of organic solvent or solvent mixture;
a capsule-forming material obtainable by curing 0.5–5% by weight of isocyanate prepolymers;
0.2–5% by weight of one or more surfactants selected from the group consisting of emulsifiers and dispersants and
an amount of calcium chloride, wherein said amount is sufficient to produce a density of the aqueous phase of between 1.05 and 1.45 kg/l.

2. The microcapsule dispersion as claimed in claim 1, wherein the isocyanate prepolymer is an oil-soluble industrial mixed product of polyisocyanates based on condensates of aniline and formaldehyde.

3. The microcapsule dispersion as claimed in claim 1, wherein the capsule-forming material was obtained by curing the isocyanate prepolymers in the presence of water at 0–95° C. or with the required amount of a diamine.

4. The microcapsule dispersion as claimed in claim 1, wherein the capsule-forming material is obtainable by curing the isocyanate prepolymers with up to three times the stoichiometric amount of a diamine.

5. The microcapsule dispersion as claimed in claim 1, wherein the density of the aqueous phase is between 1.10 to 1.40 kg/l.

6. The microcapsule dispersion as claimed in claim 1, wherein the density of the aqueous phase is between 1.15 to 1.35 kg/l.

7. The microcapsule dispersion as claimed in claim 1 wherein the capsule-forming material is obtainable by curing the isocyanate prepolymers in the presence of water at 20–65° C.

8. An aqueous endosulfan microcapsule dispersion in which the dispersed microcapsules comprise endosulfan, an organic solvent or solvent mixture and a capsule-forming material based on isocyanate prepolymers and the aqueous phase, which represents the dispersion medium, comprises surfactants with or without other formulation aids, and which microcapsule dispersion, based on the total dispersion, comprises:

20–35% by weight of endosulfan;
15–30% by weight of organic solvent or solvent mixture;
capsule-forming material obtainable by curing 1–2% by weight of isocyanate prepolymers;
0.5–2% by weight of one or more surfactants selected from the group consisting of emulsifiers and dispersants; and
an amount of calcium chloride, wherein said amount is sufficient to produce a density of the aqueous phase of between 1.05 and 1.45 kg/l.

9. A process for preparing an aqueous endosulfin microcapsule dispersion in which the dispersed microcapsules comprise endosulfan, an organic solvent or solvent mixture and a capsule-forming material based on isocyanate prepolymers and the aqueous phase, which represents the dispersion medium, comprises surfactants with or without other formulation aids, and which microcapsule dispersion comprises, based on the total dispersion, 20–40% by weight of endosulfan;
10–35% by weight of organic solvent or solvent mixture;
a capsule-forming material obtainable by curing 0.5–5% by weight of isocyanate prepolymers;

0.2–5% by weight of one or more surfactants selected from the group consisting of emulsifiers and dispersants; and an amount of calcium chloride, wherein said amount is sufficient to produce a density of the aqueous phase of between 1.05 and 1.45 kg/l, mwhich comprises preparing a coarse preemulsion of an organic and aqueous phase, then subjecting this to shear forces and, with or without addition of a diamine, curing the fine emulsion thus obtained in the entire volume of substance.

* * * * *